United States Patent
Rodgers et al.

(10) Patent No.: US 7,176,183 B2
(45) Date of Patent: *Feb. 13, 2007

(54) METHODS FOR TREATING AND PREVENTING DAMAGE TO MUCOSAL TISSUE

(75) Inventors: Kathleen E. Rodgers, Long Beach, CA (US); Gere S. diZerega, Pasadena, CA (US)

(73) Assignee: University of Southern California, Los Angeles, CA (US)

(*) Notice: Subject to any disclaimer, the term of this patent is extended or adjusted under 35 U.S.C. 154(b) by 28 days.

This patent is subject to a terminal disclaimer.

(21) Appl. No.: 10/875,155

(22) Filed: Jun. 23, 2004

(65) Prior Publication Data

US 2005/0004036 A1    Jan. 6, 2005

Related U.S. Application Data

(63) Continuation of application No. 09/723,257, filed on Nov. 27, 2000, now Pat. No. 6,821,953.

(60) Provisional application No. 60/213,224, filed on Jun. 19, 2000, provisional application No. 60/171,249, filed on Dec. 16, 1999.

(51) Int. Cl.
  *A61K 38/08* (2006.01)
(52) U.S. Cl. .................. 514/16; 514/17; 530/316; 530/329; 530/330
(58) Field of Classification Search .............. 514/16, 514/17; 530/316, 329, 330
  See application file for complete search history.

(56) References Cited

U.S. PATENT DOCUMENTS

| | | | |
|---|---|---|---|
| 4,377,573 A | 3/1983 | LeVeen | |
| 5,015,629 A | 5/1991 | diZerega et al. | |
| 5,567,733 A | 10/1996 | Dishler | |
| 5,629,292 A | 5/1997 | Rodgers et al. | |
| 5,716,935 A | 2/1998 | Rodgers et al. | |
| 5,906,811 A | 5/1999 | Hersh | |
| 5,972,887 A | 10/1999 | Schwartz | |
| 5,981,499 A | 11/1999 | Hau | |
| 6,096,709 A | 8/2000 | Rodgers et al. | |
| 6,110,895 A | 8/2000 | Rodgers et al. | |
| 6,165,978 A | 12/2000 | Rodgers et al. | |

(Continued)

FOREIGN PATENT DOCUMENTS

EP    0 187 956    7/1986

(Continued)

OTHER PUBLICATIONS

U.S. Appl. No. 10/842,877, filed May 2004, Rodgers et al.*

(Continued)

*Primary Examiner*—Jon Weber
*Assistant Examiner*—Rosanne Kosson
(74) *Attorney, Agent, or Firm*—McDonnell Boehnen Hulbert & Berghoff LLP

(57) ABSTRACT

The present invention provides improved methods, kits, and pharmaceutical compositions for treating and preventing damage to mucosal tissue by administering an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists to the subject.

7 Claims, 1 Drawing Sheet

U.S. PATENT DOCUMENTS

| | | |
|---|---|---|
| 6,177,407 B1 | 1/2001 | Rodgers et al. |
| 6,239,109 B1 | 5/2001 | Rodgers et al. |
| 6,248,587 B1 | 6/2001 | Rodgers et al. |
| 6,335,195 B1 | 1/2002 | Rodgers et al. |
| 6,455,500 B1 * | 9/2002 | Rodgers et al. ............... 514/16 |
| 6,482,800 B1 | 11/2002 | Rodgers et al. |
| 6,498,138 B1 | 12/2002 | Rodgers et al. |
| 6,762,167 B1 * | 7/2004 | Rodgers et al. ............... 514/16 |
| 6,821,953 B1 * | 11/2004 | Rodgers et al. ............... 514/16 |

FOREIGN PATENT DOCUMENTS

| | | |
|---|---|---|
| WO | WO 96/14858 | 5/1996 |
| WO | WO 99/43339 | 9/1999 |

OTHER PUBLICATIONS

Pfeilschifter, et al., (1992), Eur. J. Pharmacol., 225: pp. 57-62.

Jaiswal, et al., (1992), Hypertension 19 (Supp. II): II-49 II-55.

Jaiswal, et al., (1991), J. Pharmacol. Exper. Ther. 265: pp. 664-673.

Jaiswal, et al., (1991), Hypertension, 17: pp. 1115-1120.

Edwards and Stack, (1993), J. Pharmacol. Exper. Ther. 266: pp. 506-510.

Portsi, et al., (1994), Br. J. Pharmacol., 111: pp. 652-654.

Ferrario, et al., (1998), J. Am. Soc. Nephrol., 9: pp. 1716-1722.

Ferrario, et al., (1997), Hypertension, vol. 30(3): pp. 535-541.

Iyer et al., (1998), Hypertension, 31: pp. 699-705.

Freeman, et al., (1996), Hypertension, 28: pp. 104.

Ambuhl, et al., (1994) Brain Res. Bull., 35: pp. 289.

Ohkubo, et al., (1994), Am. J. Respir. Cell Mol. Biol., vol. 11, pp. 173-180.

* cited by examiner

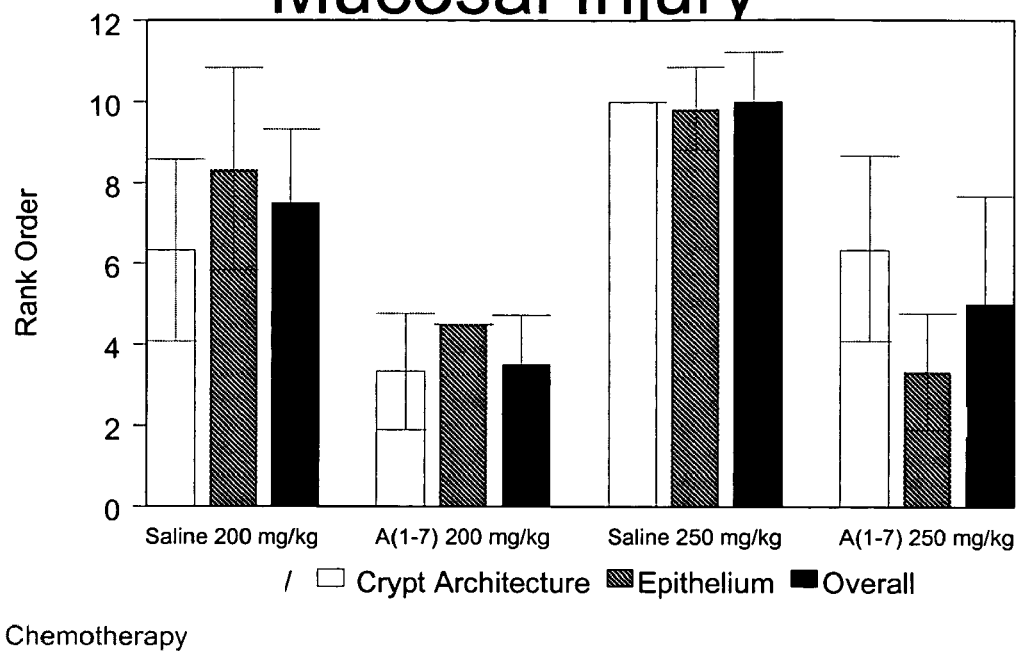

METHODS FOR TREATING AND PREVENTING DAMAGE TO MUCOSAL TISSUE

CROSS REFERENCE

This application is a continuation of application Ser. No. 09/723,257, filed Nov. 27, 2000, now U.S. Pat. No. 6,821,953, and claims priority to U.S. Provisional Patent Application Nos. 60/171,249, filed on Dec. 16, 1999, and 60/213,224, filed on Jun. 19, 2000. This Application is related to copending and commonly owned patent applications 09/264,563, filed on Mar. 8, 1999, now U.S. Pat. No. 6,455,500; and Ser. No. 09/287,674 filed on Apr. 7, 1999, abandoned; and Ser. No. 09/307,940, filed on May 10, 1999, now U.S. Pat. No. 6,475,988.

FIELD OF THE INVENTION

This present invention relates to methods to treat and prevent damage to mucosal tissue.

BACKGROUND OF THE INVENTION

Mucous membranes (or mucosa) typically possess an epithelial layer beneath which is a lamina propria rich in seromucous glands and a dense network of small blood vessels. (Ohkubo et al., Am. J. Respir. Cell Mol. Biol. 11:173–180 1994).

The present invention provides methods, pharmaceutical compositions, and kits for treating and preventing damage to mucosal tissue, comprising administering to a subject in need thereof an amount effective to treat or prevent damage to mucosal tissue of at least one active agent of the invention. The mucosal tissue to be treated is preferably selected from oral, buccal, sublingual, nasal, vaginal, rectal, aural, lung, and gastrointestinal mucosa. Examples of damage to mucosal tissue are provided below.

Mucosal ulcers of the mouth, commonly referred to as aphthous stomatitis, aphthous ulcers, or canker sores often appear on the unkeratinized oral mucosal surface of the soft palate, the ventral or lateral tongue, the buccal-labial mucosa, or the floor of the mouth. (U.S. Pat. No. 5,981,499, herein incorporated by reference in its entirety.) Small aphthous ulcers usually heal spontaneously in one to three weeks, but larger ulcers may require months to resolve, often with scarring.

Aphthous-like ulcers can be associated with allergic reactions, human immunodeficiency virus and herpes simplex virus infection, menstrual cycles, prolonged fever, emotional stress, local trauma, low serum iron, ferritin or zinc levels, deficiency of vitamin $B_{12}$, malabsorption in association with celiac or Crohn's disease, food hypersensitivity, and drug reactions.

The first stage of an emerging canker is a vesicle in the stratum granulosum of the mucosal squamous epithelium, produced by intraepithelial edema. (U.S. Pat. No. 5,981,499) The painful symptoms of the ulcer do not occur until the vesicle breaks, presenting an area of ulceration which disrupts the normal epithelium of the mucosa. Once an ulcer forms, the mucosa is no longer protected by an intact epithelium and the raw surface of the ulcer is exposed to the microorganisms that normally inhabit the oral cavity.

Examples of indigenous oral flora include lactobacilli, actinomyces, leptotrichiae, α-hemolytic *streptococci*, *enterococci*, gram-positive *cocci*, Neisseriae, diphtheroid *bacilli*, fusiform *bacilli*, bacteroides, *spirochetes*, yeasts and *Candida*. (U.S. Pat. No. 5,981,499) When existent in normally balanced proportions, these microorganisms do not usually produce disease in the intact oral mucosa of a healthy person. However, upon rupture of a canker ulcer, opportunistic pathogens quickly destroy the remnants of the local surface barrier of the oral mucosa. The result is a secondary infection, characterized by a dense acute and a chronic inflammatory cell infiltration of the exposed connective tissue of the lamina propria mucosae at the crater of the ulcer.

Despite the multifactorial etiology of aphthous ulcers, secondary infections arise after rupture of the intraepithelial vesicle during the early development of all cankers. Control of infection is essential for promoting the healing process. (U.S. Pat. No. 5,981,499)

The treatment of aphthous stomatitis to date has been palliative, using various measures to lessen the pain, to control secondary infection, and to reduce inflammatory reaction after the painful ulcer is established. The treatments of choice for aphthous ulcers have varied over the years, but in general, palliative treatments have met with only limited success.

In another example, leukoplakia is a localized irritation of the buccal mucosa due to direct contact of smoked or smokeless tobacco. (U.S. Pat. No. 5,906,811; incorporated by reference herein in its entirety.) Although leukoplakia is a benign oral lesion, it has a malignant potential, requiring a biopsy of the lesion to rule out cancer. Leukoplakia may regress or resolve completely when use of tobacco products is discontinued.

Other examples of damage to mucosal tissue include oral mucositis, burning mouth syndrome, lichen planus, denture sores, gingivitus, recent oral surgical sites, cervical dysplasia, vulva leukoplakia and other vulval lesions, Bechets Syndrome, radiotherapy induced mucositis, post-operative gum pain, traumatic mouth lesions, post-radiotherapy vaginitis, non-specific vaginal inflammatory conditions, other viral auto-immune and inflammatory ulcerations of the mucosa, nonspecific ulcer of colon, ulcerative colitis induced by nonspecific inflammations, and Crohn's disease. (See U.S. Pat. Nos. 5,972,906 and 5,576,331, both references incorporated by reference herein in their entirety.)

Thus, methods to prevent and/or treat damage to mucosal tissue would be of great utility.

SUMMARY OF THE INVENTION

The present invention provides methods and kits for treating or preventing damage to mucosal tissue by contacting the mucosal tissue with an amount effective to treat or prevent damage to mucosal tissue of angiotensinogen, angiotensin I (AI), AI analogues, AI fragments and analogues thereof, angiotensin II (AII), AII analogues, AII fragments or analogues thereof, or AII $AT_2$ type 2 receptor agonists, either alone, combined, or in further combination with other mucosal-protecting compounds, including anti-inflammatory drugs, angiotensin converting enzyme (ACE) inhibitors, anti-infectives, growth factors, and antihistamines.

BRIEF DESCRIPTION OF THE FIGURES

FIG. 1. Effect of angiotensin peptides on mucosal injury

DETAILED DESCRIPTION OF THE PREFERRED EMBODIMENTS

All cited patents, patent applications and references are hereby incorporated by reference in their entirety.

Unless otherwise indicated, the term "active agents" as used herein refers to the group of compounds comprising angiotensinogen, angiotensin I (AI), AI analogues, AI fragments and analogues thereof, angiotensin II (AII), AII analogues, AII fragments or analogues thereof or AII $AT_2$ type 2 receptor agonists.

Unless otherwise indicated, the term "angiotensin converting enzyme inhibitors" or "ACE inhibitors" includes any compound that inhibits the conversion of the decapeptide angiotensin I to angiotensin II, and includes but is not limited to alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. (See for example Jackson, et al., Renin and Angiotensin in Goodman & Gilman's The Pharmacological Basis of Therapeutics, 9th ed., eds. Hardman, et al. (McGraw Hill, 1996); and U.S. Pat. No. 5,977,159.)

As used herein, the term "mucosa" or "mucosal tissue" refers to the moist tissue that lines some organs and body cavities and secretes mucous, including but not limited to oral (including buccal and sublingual), nasal, vaginal, rectal, aural, lung, and gastrointestinal mucosa.

As used herein, "mucosal damage" includes, but is not limited to damage caused by bacterial, viral, and fungal infections, ulcerations, autoimmune disorders, septic shock, allergic and non-allergic rhinitis, hemorrhagic shock, endotoxemia, oral mucositis, burning mouth syndrome, lichen planus, denture sores, gingivitis, recent oral surgical sites, cervical dysplasia, vulva leukoplakia and other vulval lesions, Bechets Syndrome, radiotherapy induced mucositis, post-operative gum pain, traumatic mouth lesions, post-radiotherapy vaginitis, non-specific vaginal inflammatory conditions, and other viral auto-immune and inflammatory ulcerations of the mucosa, nonspecific ulcer of colon, ulcerative colitis induced by nonspecific inflammations, and Crohn's disease.

"Treating and preventing damage to mucosal tissue" includes the non-limiting examples of healing ulcerations, preventing or reducing inflammation and/or pain, and treating or preventing secondary infections.

We have previously demonstrated that angiotensinogen, angiotensin I (AI), AI analogues, AI fragments and analogues thereof, angiotensin II (AII), AII analogues, AII fragments or analogues thereof; AII $AT_2$ type 2 receptor agonists are effective in accelerating wound healing, treating and preventing infections, and the proliferation of certain cell types. See, for example, co-pending U.S. patent application Ser. No. 09/012,400, filed Jan. 23, 1998; Ser. No. 09/198,806 filed Nov. 24, 1998; Ser. No. 09/264,563, filed Mar. 8, 2000; Ser. No. 09/287,674, filed Apr. 7, 1999; Ser. No. 09/255,136 filed Feb. 19, 1999; Ser. No. 09/245,680, filed Feb. 8, 1999; Ser. No. 09/250,703 filed Feb. 15, 1999; Ser. No. 09/246,525 filed Feb. 8, 1999; Ser. No. 09/266,293 Mar. 11, 1999; Ser. No. 09/332,582 filed Jun. 14, 1999; Ser. No. 09/373,962 filed Aug. 13, 1999; and Ser. No. 09/352,191 filed Jul. 12, 1999; as well as U.S. Pat. Nos. 5,015,629; 5,629,292; 5,716,935; 5,834,432; and 5,955,430; 6,096,709; and 6,110,895.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (*Circulation Research* 60:786–790 (1987); Clouston et al., *Genomics* 2:240–248 (1988); Kageyama et al., *Biochemistry* 23:3603–3609; Ohkubo et al., *Proc. Natl. Acad. Sci.* 80:2196–2200 (1983)); all references hereby incorporated in their entirety). The substance so formed is a decapeptide called angiotensin I (AI) which is converted to AII by the ACE angiotensinase, which removes the C-terminal His-Leu residues from AI, Asp-Arg-Val-Tyr-Ile-His-Pro-Phe-His-Leu [SEQ ID NO:37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264: 526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990)). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195: 305–6 (1991)). Additionally, AII and angiotensin III analogs and fragments thereof have been shown to be effective in tissue repair. (U.S. Pat. No. 5,629,292; International Application No. WO 95/08565; International Application WO 95/08337; International Application No. WO 96/39164; all references hereby incorporated in their entirety.) AII has also been shown to increase cellular proliferation in hair follicles in the area of a thermal injury. (Rodgers et al., J. Burn Care Rehabil. 18:381–388 (1997)).

The effect of AII on a given cell type has been hypothesized to be dependent, in part, upon the AII receptor subtypes the cell expresses (Shanugam et al., *Am. J. Physiol.* 268:F922–F930 (1995); Helin et al., *Annals of Medicine* 29:23–29 (1997); Bedecs et al., *Biochem J.* 325:449–454 (1997)). These studies have shown that AII receptor subtype expression is a dynamic process that changes during development, at least in some cell types. AII activity is typically modulated by either or both the AT1 and AT2 AII receptors. However, AII has recently been shown to stimulate proliferation of primary human keratinocytes via a non-AT1, non-AT2 receptor. (Steckelings et al., Biochem. Biophys. Res. Commun. 229:329–333 (1996)). These results underscore the cell-type (ie: based on receptor expression) specific nature of AII activity.

Many studies have focused upon AII(1–7) (AII residues 1–7) or other fragments of AII to evaluate their activity. AII(1–7) elicits some, but not the full range of effects elicited by AII. (Pfeilschifter, et al., *Eur. J. Pharmacol.* 225:57–62 (1992); Jaiswal, et al., *Hypertension* 19(Supp. II):II-49–II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et al., *Br. J. Pharmacol.* 111:652–654 (1994)).

Other data suggest that the AII fragment AII(1–7) acts through a receptor(s) that is distinct from the AT1 and AT2 receptors that modulate AII activity. (Ferrario et al., J. Am. Soc. Nephrol. 9:1716–1722 (1998); Iyer et al., Hypertension 31:699–705 (1998); Freeman et al., Hypertension 28:104 (1996); Ambuhl et al., Brain Res. Bull. 35:289 (1994). Thus, AII(1–7) activity on a particular cell type cannot be predicted based solely on the effect of AII on the same cell type. In fact, there is some evidence that AII(1–7) often opposes the actions of AII. (See, for example, Ferrario et al., Hypertension 30:535–541 (1997))

Recent reports have suggested the use of ACE inhibitors for the treatment of oral mucosal inflammation elicited by smokeless tobacco (Gao et al., J. Appl. Phys. 83(1):74–81 (1997); to protect jejunal mucosa from radiation damage (Yoon et al, Int. J. Radiation Oncol. Biol. Phys. 30:873–878 (1994); and to treat nasal inflammatory responses (Ohkubo et al., Am. J. Respir. Cell Mol. Biol. 11:173–180 (1994).

Based on the above, there would be no expectation by one of skill in the art that the active agents of the invention could be used to treat and prevent damage to mucosal tissue.

A peptide agonist selective for the AT2 receptor (AII has 100 times higher affinity for AT2 than AT1) is p-aminophenylalanine6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair, which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffinan, et al., *Life Sci.* 49:223–228 (1991); Viswanathan, et al., *Peptides* 13:783–786 (1992); Kimura, et al., *BBRC* 187:1083–1090 (1992).

As hereinafter defined, a preferred class of AT2 agonists for use in accordance with the present invention comprises AII, AII analogues, or active fragments thereof having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AII analogues, fragments of AII and analogues thereof of particular interest in accordance with the present invention comprise a sequence of at least three contiguous amino acids of groups $R^1$–$R^8$ in the sequence of general formula I

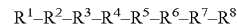

wherein $R^1$ is selected from H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, or is absent, $R^2$ is selected from Arg, Lys, Ala, Citron, Orn, Ser(Ac), Sar, D-Arg and D-Lys, $R^3$ is selected from the group consisting of Val, Ala, Leu, norLeu, Ile, Gly, Lys, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

In alternate embodiments, the active agents comprise a sequence of at least four, five, six, or seven contiguous amino acids of groups $R^1$–$R^8$ in the sequence of general formula I. In a further alternative, the active agents consist essentially of a sequence of at least four, five, six, or seven contiguous amino acids of groups $R^1$–$R^8$ in the sequence of general formula I.

Compounds falling within the category of AT2 agonists useful in the practice of the invention include the AII analogues set forth above subject to the restriction that $R^6$ is p-NH$_2$-Phe.

Particularly preferred combinations for $R^1$ and $R^2$ are Asp-Arg, Asp-Lys, Glu-Arg and Glu-Lys. Particularly preferred embodiments of this class comprise the following sequences: AII [SEQ ID NO: 1], AIII or AII(2–8), Arg-Val-Tyr-Ile-His-Pro-Phe [SEQ ID NO:2]; AII(3–8), also known as desl-AIII or AIV, Val-Tyr-Ile-His-Pro-Phe [SEQ ID NO:3]; AII(1–7), Asp-Arg-Val-Tyr-Ile-His-Pro [SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII(4–8), Tyr-Ile-His-Pro-Phe [SEQ ID NO: 15] were also tested and found not to be effective.

Another class of compounds of particular interest in accordance with the present invention are those of the general formula II

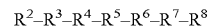

in which $R^2$ is selected from the group consisting of H, Arg, Lys, Ala, Orn, Citron, Ser(Ac), Sar, D-Arg and D-Lys;

$R^3$ is selected from the group consisting of Val, Ala, Leu, norLeu, Ile, Gly, Lys, Pro, Aib, Acpc and Tyr;

$R^4$ is selected from the group consisting of Tyr, Tyr(PO$_3$)$_2$, Thr, Ser, homoSer, azaTyr, and Ala;

$R^5$ is selected from the group consisting of Ile, Ala, Leu, norLeu, Val and Gly;

$R^6$ is His, Arg or 6-$NH_2$-Phe;

$R^7$ is Pro or Ala; and $R^8$ is selected from the group consisting of Phe, Phe(Br), Ile and Tyr.

A particularly preferred subclass of the compounds of general formula II has the formula $R^2$–$R^3$-Tyr-$R^5$-His-Pro-Phe[SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

Other particularly preferred embodiments include:

| | | | |
|---|---|---|---|
| 1GD | Ala4-AII(1–7) | DRVAIHP | SEQ ID NO: 38 |
| 2GD | Pro3-AII(1–7) | DRPYIHP | SEQ ID NO: 39 |
| 5GD | Lys3-AII(1–7) | DRKYIHP | SEQ ID NO: 40 |
| 9GD | NorLeu-AII (1–7) | DR(nor)YIHP | SEQ ID NO: 41 |
| GSD 28 | Ile⁸-AII | DRVYIHPI | SEQ ID NO: 42 |
| | Ala3aminoPhe6 AII: | RVAIHPF | SEQ ID NO: 43 |
| | Ala3-AIII | RVAIHPF | SEQ ID NO: 44 |
| | Gly¹-AII | GRVYIHPF | SEQ ID NO: 45 |
| | NorLeu⁴-AIII | --RVYnLHPF | SEQ ID NO: 46 |
| | Acpc³-AII | DR(Acpc)YIHPF | SEQ ID NO: 47 |
| GSD 37B | Orn²-AII | D(Orn)VYIHPF | SEQ ID NO: 48 |
| GSD 38B | Citron²-AII | D(Citron)VYIHPF | SEQ ID NO: 49 |
| 3GD | Pro³Ala⁴-AII (1–7) | DRPAIHP | SEQ ID NO: 50 |

In the above formulas, the standard three-letter abbreviations for amino acid residues are employed. In the absence of an indication to the contrary, the L-form of the amino acid is intended. Other residues are abbreviated as follows:

TABLE 1

| Abbreviation for Amino Acids | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Cit | Citron |
| Orn | Ornithine |

It has been suggested that AII and its analogues adopt either a gamma or a beta turn (Regoli, et al., *Pharmacological Reviews* 26:69 (1974)). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$. Alternatively, $R_2$ may be H, Ala, Orn, Citron, Ser(Ac), Sar, D-Arg, or D-Lys.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Lys, Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, and Val.

A class of active agents of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro or Ala in order to provide the most desirable orientation of $R^8$. In position $R^8$, both a hydrophobic ring and an anionic carboxyl terminal appear to be particularly useful in binding of the analogues of interest to receptors; therefore, Tyr, Ile, Phe(Br), and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by any conventional method, including, but not limited to, those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides,* Vol. 2, Academic Press, New York, (1973) for solid phase synthesis and E. Schroder and K. Lubke, *The Peptides,* Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Alternatively, the peptides may be produced via conventional molecular biological methods.

In one aspect of the present invention, a method of treating or preventing damage to mucosal tissue is provided, comprising contacting a subject in need thereof with an amount effective to treat or prevent damage to mucosal tissue of at least one compound selected from angiotensinogen, AI, AI analogues, and/or AI fragments and analogues thereof, AII, AII analogues, AII fragments and analogues thereof, and/or AII AT$_2$ type 2 receptor agonists (hereinafter referred to as the "active agents"), alone or in combination with other compounds that are beneficial to treating and preventing damage to mucosal tissue, and/or to reduce inflammation and infection. Examples of such other compounds include anti-inflammatory drugs, angiotensin converting enzyme (ACE) inhibitors, anti-infectives, growth factors, and antihistamines.

The methods of the invention are useful in any situation in which it is desired to treat or prevent damage to mucosal tissue. Specific examples of disease and/or injury conditions that can benefit from the methods of the invention include, but are not limited to damage caused by bacterial, viral, and fungal infections, ulcerations, autoimmune disorders, septic shock, allergic and non-allergic rhinitis, hemorrhagic shock, endotoxemia, oral mucositis, burning mouth syndrome, lichen planus, denture sores, gingivitus, recent oral surgical sites, cervical dysplasia, vulva leukoplakia and other vulval lesions, Bechets Syndrome, radiotherapy induced mucositis, post-operative gum pain, traumatic mouth lesions, post-radiotherapy vaginitis, non-specific vaginal inflammatory conditions, and other viral auto-immune and inflammatory ulcerations of the mucosa, nonspecific ulcers of the colon, ulcerative colitis induced by nonspecific inflammations, and Crohn's disease.

For use in treating or preventing damage to mucosal tissue, the active agents may be administered by any suitable route, but are preferably administered either orally, parentally, by inhalation spray, transdermally, rectally, buccally, vaginally, or topically in dosage unit formulations containing conventional pharmaceutically acceptable carriers, adjuvants, and vehicles. The term parenteral as used herein includes, subcutaneous, intravenous, intraarterial, intramuscular, intrastemal, intratendinous, intraspinal, intracranial, intrathoracic, infusion techniques or intraperitoneally.

In a preferred embodiment for topical application to the oral mucosa, a powder, or preferably, a troche is used. (See U.S. Pat. No. 5,981,499; incorporated by reference herein in its entirety) The troche or powder includes a dry dosage of active agent which, when applied topically, delivers the active agent directly to the mucosa.

Alternatively, the active agent may be administered to the mucosal tissue by any other convenient mode such as, for example, by lavage, by catheter, by coating directly on the mucosal site in a salve, ointment, gel, cream, aqueous surface active composition, mouthwash, toothpaste, emulsion, suspension, film, or foam. The site can be contacted directly, as by applying a salve, ointment, gel, mouthwash or toothpaste, or in some cases the medicament can be introduced to a site near the site of the wound and natural migration of fluids will serve to carry the medicament to the desired site.

The active agent may also be administered directly to a targeted mucosal tissue in a suitable vehicle, for example, a solution of 5% DMSO or 10% ethanol in saline, to a site in need thereof. In a preferred embodiment, multiple administrations of the active agents are made over the period of time encompassing wound healing.

The active agent may also be administered in a single dose delivery using a drug-delivery system that enables the maintenance of requisite concentrations of the compound for a period of time sufficient for treating or preventing damage to mucosal tissue. A suitable drug-delivery system would itself be essentially non-inflammatory and non-immunogenic and would permit release of the active agent so as to maintain effective levels thereof over the desired time period.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; crystalloid and viscous instillates; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacryladmide hydrogels, anionic carbohydrate polymers, etc. Useful delivery systems are well known in the art and are described in, e.g., U.S. Pat. No. 4,937,254, the entire disclosure of which is hereby incorporated by reference.

The active agent may be made up in a solid form (including granules, powders or suppositories) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, co-solvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the active agent is ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

For application to the rectal or vaginal mucosa, suitable compositions for use according to the invention include suppositories (emulsion or suspension type), solutions, enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives such as enhancers or surfactants may be incorporated.

For application to the nasal and upper respiratory tract mucosa, direct delivery systems are preferred. These include but are not limited to intra-oral sprays, mists, metered dose inhalers, nebulizers, and aerosols. In a typical nasal formulation, the active agent(s) is dissolved or dispersed in a suitable vehicle. The pharmaceutically acceptable vehicles and excipients and (optionally) other pharmaceutically acceptable materials present in the composition (such as diluents, enhancers, flavouring agents, and preservatives) are all selected in accordance with conventional pharmaceutical practice, in a manner understood by the persons skilled in the art of formulating pharmaceuticals.

For application to the skin or nail, the active agents for use according to the invention may contain conventionally non-toxic pharmaceutically acceptable carriers and excipients including microspheres and liposomes. The formulations include creams, ointments, lotions, liniments, gels, hydrogels, solutions, suspensions, sticks, sprays, and pastes. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

The dosage regimen for treating or preventing damage to mucosal tissue with the active agent is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg, preferably about 1 ng/kg to about 1 mg/kg, more preferably about 100 ng/kg to about 500 µg/kg, even more preferably about 1 µg/kg to about 100 µg/kg of the active agents per body weight are useful for all methods of use disclosed herein.

In a further aspect, the present invention provides kits for treating or preventing damage to mucosal tissue, wherein the kits comprise an effective amount of the active agent to treat or prevent damage to mucosal tissue, and instructions for using the amount effective of active agent to treat or prevent damage to mucosal tissue. In a preferred embodiment, the kits also contain an effective amount to treat or prevent damage to mucosal tissue, and/or to reduce inflammation and infection, of one or more other compounds that accelerate wound healing and/or cell proliferation. Examples of such other compounds include anti-inflammatory drugs, angiotensin converting enzyme (ACE) inhibitors, anti-infectives, growth factors, and antihistamines.

In another aspect of the invention, pharmaceutical compositions are provided that comprise an amount effective for treating or preventing damage to mucosal tissue of the active agents of the invention, alone or in combination with an amount effective to aid in treating or preventing damage to mucosal tissue, and/or to reduce inflammation and infection, of a compound selected from the group consisting of anti-inflammatory drugs, angiotensin converting enzyme (ACE) inhibitors, anti-infectives, growth factors, and antihistamines.

The methods of the present invention will be clinically useful in any situation where it is desired to treat or prevent mucosal damage. Examples of such situations include but are not limited to mucosal damage caused by bacterial, viral, and fungal infections, mucosal ulcerations, autoimmune disorders, septic shock, allergic and non-allergic rhinitis, hemorrhagic shock, endotoxemia, oral mucositis, burning mouth syndrome, lichen planus, denture sores, gingivitis, recent oral surgical sites, cervical dysplasia, vulva leukoplakia and other vulval lesions, Bechets Syndrome, radiotherapy induced mucositis, post-operative gum pain, traumatic mouth lesions, post-radiotherapy vaginitis, non-specific vaginal inflammatory conditions, and other viral auto-immune and inflammatory ulcerations of the mucosa, nonspecific ulcer of colon, ulcerative colitis induced by nonspecific inflammations, and Crohn's disease.

EXAMPLE 1

Phase I/II Dose Escalation Study of Angiotensin II 1–7 (AII(1–7) SEQ ID NO:4) Administered Before and After Chemotherapy in Patients with Newly Diagnosed Breast Cancer The Phase I/II study was a prospective, open-label, dose-escalation study comparing the effects of AII(1–7 (SEQ ID NO:4)) in patients with newly diagnosed breast cancer receiving doxorubicin 60 mg/m$^2$ and cyclophosphamide 600 mg/m$^2$ for at least 3 cycles of adjuvant chemotherapy following surgical tumor reduction. A filgrastim comparator arm was used to compare safety and response variables and to assess synergy of AII(1–7) with filgrastim (NEUPOGEN®, Amgen, Inc., Thousand Oaks, Calif.).

Patients who satisfied the inclusion/exclusion criteria received a once daily subcutaneous injection of the given AII(1–7) dose level for 7 days followed by a 1 week rest period prior to any chemotherapy (cycle 0) in the interval between tumor reduction and planned chemotherapy. Dose escalation within an individual patient was not permitted.

Following the rest period, a chemotherapy regimen containing doxorubicin 60 mg/m$^2$ and cyclophosphamide 600 mg/m$^2$ was initiated. AII(1–7) was administered for at least 10 days, or until the absolute neutrophil count (ANC)>1500/μL for 2 days, beginning two days after chemotherapy. Up to three chemotherapy cycles followed by AII(1–7) administration will be repeated every 21 days or as indicated by patient tolerance. Any patient that fails to achieve an ANC>1500/μL by day 15 (13 days of AII(1–7)) received a filgrastim rescue of 5.0 μg/kg/day until the ANC>1500/μL for 2 days.

AII(1-7) (SEQ ID NO:4) Arm

| | |
|---|---|
| Group 1: | 2.5 μg/kg/day AII(1-7) (0.25 mg/mL) |
| Group 2: | 10.0 μg/kg/day AII(1-7) (1.0 mg/mL) |

-continued

| | |
|---|---|
| Group 3: | 25.0 μg/kg/day AII(1-7) (5.0 mg/mL) |
| Group 4: | 50.0 μcg/kg/day AII(1-7) (5.0 mg/mL) |
| Group 5: | 75.0 μg/kg/day AII(1-7) (10.0 mg/mL) |
| Group 6: | 100.0 μg/kg/day AII(1-7) (10.0 mg/mL) |
| Filgrastim Arm: | |
| Filgrastim | 5.0 μg/kg/day |

During the conduct of the AII (1–7) clinical trial to examine the effect of subcutaneous injection of AII(1–7) on hematological recovery in new breast cancer patients receiving chemotherapy (doxorubicin/cyclophosphamide), adverse events that occurred were collected.

An adverse event (AE) was considered any unfavorable or unintended change in structure, function, signs, or symptoms temporally associated with the use of a medicinal product experienced by a person administered a pharmaceutical product, whether or not a causal relationship with the product has been established. During the conduct of this clinical trial, study personnel asked open-ended questions to obtain information about AEs at every visit. Signs and symptoms were graded by the Investigator using the WHO toxicity criteria. Stomatitis (oral mucositis) was shown to be reduced in this clinical trial by subcutaneous administration of AII(1–7). If there was stomatitis, it was graded on a four point scale as:

| Grade | Description |
|---|---|
| 1 | Painful ulcers, erythema, or mild soreness in the absence of lesions |
| 2 | Painful erythema, edema or ulcers, but can eat or swallow |
| 3 | Painful erythema, edema or ulcers requiring IV hydration |
| 4. | Severe ulceration or requires parenteral or enteral nutritional support or prophylactic intubation |

In this trial, the incidents of stomatitis associated with chemotherapy were as follows:

| | Treatment Group | | |
|---|---|---|---|
| | Historic | AII(1-7) (n = 14) | Filgratim (n = 5) |
| Stomatitis | 88% | 40% | 60% |

Thus, AII(1–7) significantly decreased stomatitis in chemotherapy patients relative to control. Additionally, AII (1–7) reduced the frequency of stomatitis by 30% of that observed with filgrastim treatment.

EXAMPLE 2

Effect of Active Agents on Gastrointestinal Mucositis Induced by Cyclophopphamide Injection Into Mice Female C57B1/6 mice were given an intraperitoneal injection of cyclophosphamide at concentrations of 200 or 250 mg/kg. After 2 days, the mice began treatment with either AII(1–7) (100 μg/kg), or phosphate buffered saline, both of which were given subcutaneously. The baseline weight of the mice was determined, and the mice were observed daily for 7–14 days, after which the animals were necropsied. Samples from the intestines were taken at four levels, in that the intestine was cut transversely at four places along the intestinal tract, from which histological preparations were made and evaluated, in order to reduce bias due to site selection. The samples were fixed in formalin for histological evaluation of crypt distortion and architecture, as well as epithelial attenuation. The crypt is a part of the gastrointestinal tract where the mucosal glands reside. Crypt distortion is a measure of the amount of disruption to the tissue that occurs as a result of mucosal damage. The epithelium is the cell/mucosal lining to the gastrointestinal tract. Epithelial attenuation is a measure of the amount of destruction to the epithelial lining.

Histological scoring was performed in a blinded fashion. The scores on the accompanying table were given on the following scale:

Crypt Architecture:

| | |
|---|---|
| 0 | Normal |
| 1 | <10% Crypt distortion |
| 2 | 10–50% Crypt distortion |
| 3 | >50% Crypt distortion |

Epithelium

| | |
|---|---|
| 0 | Normal |
| 1 | Mild Attenuation (<10%) |
| 2 | Moderate Attenuation (10–50%) |
| 3 | Severe Attenuation (>50%) |

Overall Score

| | |
|---|---|
| 0 | No lesion |
| 1 | <10% Crypts distorted |
| 2 | >10% Crypts distorted, no necrotic cells |
| 3 | >10% Crypts distorted, occasional necrotic cell |
| 4 | Same as 3 except more extensive |

As can be seen in Table 1, administration of AII(1–7) reduced the level of gastrointestinal mucositis by all histological scores.

| Mucositis Group | Crypt Architecture | Epithelium | Overall |
|---|---|---|---|
| Saline 200 | 1 | 1 | 1 |
| Saline 200 | 1 | 2 | 2 |
| Saline 200 | 2 | 3 | 2 |
| A(1-7) 200 | 0 | 1 | 0 |
| A(1-7) 200 | 1 | 1 | 1 |
| A(1-7) 200 | 1 | 1 | 1 |
| Saline 250 | 2 | 2 | 2 |
| Saline 250 | 2 | 2 | 2 |
| Saline 250 | 2 | 3 | 3 |
| A(1-7) 250 | 1 | 0 | 0 |
| A(1-7) 250 | 1 | 1 | 1 |
| A(1-7) 250 | 2 | 1 | 2 |

As these data are non parametric, the ranks of the scores were taken and are shown on FIG. 1.

---

We claim:

1. A method for treating damage to mucosal tissue, comprising administering to a subject in need thereof an amount effective for treating damage to mucosal tissue of at least one active agent comprising a sequence consisting of at least five contiguous amino acids of SEQ ID NO:4, wherein the mucosal damage is associated with bacterial infection, viral infection, fungal infections, ulcerations, autoimmune disorders, septic shock, allergic and non-allergic rhinitis, hemorrhagic shock, endotoxemia, cervical dysplasia, vulva leukoplakia, Bechets Syndrome, chemotherapy induced mucositis, post-radiotherapy vaginitis, non-specific vaginal inflammatory conditions, gastrointestinal mucositis, and Crohn's disease.

2. The method of claim 1 wherein the method is used to treat chemotherapy-induced mucositis.

3. The method of claim 1 wherein the method is used to treat gastrointestinal mucositis.

4. The method of claim 1 wherein the active agent comprises a sequence consisting of at least six contiguous amino acids of SEQ ID NO:4.

5. The method of claim 1 wherein the active agent comprises a sequence consisting of SEQ ID NO:4.

6. The method of claim 5 wherein the method is used to treat chemotherapy-induced mucositis.

7. The method of claim 5 wherein the method is used to treat gastrointestinal mucositis.

* * * * *

SEQUENCE LISTING

<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:
    Synthetic AII sequence

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:
    Synthetic AII (2-8) sequence

<400> SEQUENCE: 2

Arg Val Tyr Ile His Pro Phe
 1               5

<210> SEQ ID NO 3
<211> LENGTH: 6

-continued

```
<212> TYPE: PRT
<213> ORGANISM: Artificial Sequence
<220> FEATURE:
<223> OTHER INFORMATION: Description of Artificial Sequence:
      Synthetic AII (3-8) sequence

<400> SEQUENCE: 3

Val Tyr Ile His Pro Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:
      Synthetic AII (1-7) sequence

<400> SEQUENCE: 4

Asp Arg Val Tyr Ile His Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:
      Synthetic AII (2-7) sequence

<400> SEQUENCE: 5

Arg Val Tyr Ile His Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:
      Synthetic AII (3-7) sequence

<400> SEQUENCE: 6

Val Tyr Ile His Pro
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:
      Synthetic AII (5-8) sequence

<400> SEQUENCE: 7

Ile His Pro Phe
1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:
      Synthetic AII (1-6) sequence

<400> SEQUENCE: 8

Asp Arg Val Tyr Ile His
```

```
                        1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      Synthetic AII (1-5) sequence

<400> SEQUENCE: 9

Asp Arg Val Tyr Ile
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
      Synthetic AII (1-4) sequence

<400> SEQUENCE: 10

Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:
      Synthetic AII (1-3) sequence

<400> SEQUENCE: 11

Asp Arg Val
  1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:
      Synthetic AII analogue sequence
<220> FEATURE:
<221> NAME/KEY: misc_feature
<222> LOCATION: (2)
<223> OTHER INFORMATION: Xaa stands for Nle

<400> SEQUENCE: 12

Arg Xaa Tyr Ile His Pro Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:
      Synthetic AII analogue sequence
<220> FEATURE:
<221> NAME/KEY: misc_feature
<222> LOCATION: (4)
<223> OTHER INFORMATION: Xaa stands for Nle

<400> SEQUENCE: 13

Arg Val Tyr Xaa His Pro Phe
  1               5
```

```
<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:
      Synthetic AII (6-8) sequence

<400> SEQUENCE: 14

His Pro Phe
 1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:
      Synthetic AII (4-8) sequence

<400> SEQUENCE: 15

Tyr Ile His Pro Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:
      Synthetic AII analogue
      class
<220> FEATURE:
<221> NAME/KEY: misc_feature
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: misc_feature
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: misc_feature
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:
      Synthetic AII analogue sequence

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
```

-continued

<223> OTHER INFORMATION: Description of Artificial Sequence:
      Synthetic AII analogue sequence

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 1 sequence

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 2 sequence

<400> SEQUENCE: 20

Asn Arg Val Tyr Val His Pro Phe
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Sy
      nthetic AII analogue 3 sequence

<400> SEQUENCE: 21

Ala Pro Gly Asp Arg Ile Tyr Val His Pro Phe
 1               5                   10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 4 sequence

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 5 sequence

<400> SEQUENCE: 23

Asp Lys Val Tyr Ile His Pro Phe
 1               5

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 6 sequence

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 7 sequence

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 8 sequence

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Sy
      nthetic AII analogue 9 sequence

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Syn
      thetic AII analogue 10 sequence

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Syn
      thetic AII analogue 11 sequence

<400> SEQUENCE: 29
```

Asp Arg Val Tyr Ile His Pro Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Syn
      thetic AII analogue 12 sequence

<400> SEQUENCE: 30

Pro Arg Val Tyr Ile His Pro Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Syn
      thetic AII analogue 13 sequence

<400> SEQUENCE: 31

Asp Arg Pro Tyr Ile His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:
      Synthetic AII analogue 14 sequence
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:
      Synthetic AII analogue 15 sequence
<220> FEATURE:
<221> NAME/KEY: misc_feature
<222> LOCATION: (3)
<223> OTHER INFORMATION: Xaa stands for Nle

<400> SEQUENCE: 33

Asp Arg Xaa Tyr Ile His Pro Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:
      Synthetic AII analogue 16 sequence
<220> FEATURE:
<221> NAME/KEY: misc_feature
<222> LOCATION: (5)

<223> OTHER INFORMATION: Xaa stands for Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:
      Synthetic AII analogue 17
      sequence
<220> FEATURE:
<221> NAME/KEY: MOD_RES
<222> LOCATION: (4)
<223> OTHER INFORMATION: homo Serine

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      p-aminophenylalanine 6 AII sequence
<220> FEATURE:
<221> NAME/KEY: misc_feature
<222> LOCATION: (6)
<223> OTHER INFORMATION: Xaa stands for p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: S
      ynthetic angiotensin I sequence

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      Synthetic 1GD:Ala4-AII(1-7) sequence

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:

```
      Synthetic 2GD
      Pro3-AII(1-7) sequence

<400> SEQUENCE: 39

Asp Arg Pro Tyr Ile His Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:
      Synthetic 5GD Lys
      3-AII(1-7) sequence

<400> SEQUENCE: 40

Asp Arg Lys Tyr Ile His Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:
      Synthetic 9GD
      Norleu-AII(1-7) sequence
<220> FEATURE:
<221> NAME/KEY: misc_feature
<222> LOCATION: (3)
<223> OTHER INFORMATION: Xaa stands for Nle

<400> SEQUENCE: 41

Asp Arg Xaa Tyr Ile His Pro
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:
      Synthetic GSD28
      Ile8-AII sequence

<400> SEQUENCE: 42

Asp Arg Val Tyr Ile His Pro Ile
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      Ala3aminoPhe6-AII sequence
<220> FEATURE:
<221> NAME/KEY: misc_feature
<222> LOCATION: (6)
<223> OTHER INFORMATION: Xaa stands for aminophenyalanine

<400> SEQUENCE: 43

Asp Arg Ala Tyr Ile Xaa Pro Phe
 1               5

<210> SEQ ID NO 44
<211> LENGTH: 7
<212> TYPE: PRT
```

-continued

```
<213> ORGANISM: Artificial Sequence
<220> FEATURE:
<223> OTHER INFORMATION: Description of Artificial Sequence:
      Synthetic Ala3-AIII sequence

<400> SEQUENCE: 44

Arg Val Ala Ile His Pro Phe
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequen
      ce: Synthetic Gly1-AII sequence

<400> SEQUENCE: 45

Gly Arg Val Tyr Ile His Pro Phe
 1               5

<210> SEQ ID NO 46
<211> LENGTH: 8
<212> TYPE: PRT
<213> ORGANISM: Artificial Sequence
<220> FEATURE:
<221> NAME/KEY: misc_feature
<222> LOCATION: (4)
<223> OTHER INFORMATION: Xaa stands for Nle
<220> FEATURE:
<223> OTHER INFORMATION: Description of Artificial Sequence:
      Synthetic Norleu4-AIII sequence

<400> SEQUENCE: 46

Arg Val Tyr Xaa Leu His Pro Phe
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:
      Synthetic Acpc3-AII sequence
<220> FEATURE:
<221> NAME/KEY: misc_feature
<222> LOCATION: (3)
<223> OTHER INFORMATION: Xaa stands for 1-aminocyclopentane
      carboxylic acid

<400> SEQUENCE: 47

Asp Arg Xaa Tyr Ile His Pro Phe
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:
      Synthetic Orn2-AII sequence
<220> FEATURE:
<221> NAME/KEY: misc_feature
<222> LOCATION: (2)
<223> OTHER INFORMATION: Xaa stands for Orn

<400> SEQUENCE: 48

Asp Xaa Val Tyr Ile His Pro Phe
 1               5
```

```
<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:
      Synthetic Citron2-AII sequence
<220> FEATURE:
<221> NAME/KEY: misc_feature
<222> LOCATION: (2)
<223> OTHER INFORMATION: Xaa stands for Citron

<400> SEQUENCE: 49

Asp Xaa Val Tyr Ile His Pro Phe
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      Pro3Ala4-AII(1-7) sequence

<400> SEQUENCE: 50

Asp Arg Pro Ala Ile His Pro
  1               5
```